United States Patent
Takekawa et al.

[11] Patent Number: 5,355,587
[45] Date of Patent: Oct. 18, 1994

[54] ULTRASONIC CUTTER

[75] Inventors: Naomitsu Takekawa, Tokyo; Yukihiro Katou, Chiba; Masahiko Yano, Shizuoka; Atsushi Horiuchi, Shizuoka; Tomoyuki Fujisaki, Shizuoka, all of Japan

[73] Assignees: Suzuki Motor Corporation, Shizuoka; Alcare Co., Ltd., Tokyo, both of Japan

[21] Appl. No.: 958,334
[22] PCT Filed: Apr. 17, 1992
[86] PCT No.: PCT/JP92/00488
§ 371 Date: Dec. 16, 1992
§ 102(e) Date: Dec. 16, 1992

[30] Foreign Application Priority Data
Apr. 17, 1991 [JP] Japan .................. 3-114073

[51] Int. Cl.5 ................ B26B 7/00; A61C 1/07
[52] U.S. Cl. ..................... 30/277.4; 433/119
[58] Field of Search ........... 30/272, 277, 168, 277.4; 173/90; 81/463; 433/86, 119, 141, 165, 188, 215

[56] References Cited
U.S. PATENT DOCUMENTS

| | | | |
|---|---|---|---|
| 2,129,843 | 9/1938 | Hollmann | 433/165 |
| 2,990,616 | 7/1961 | Balamuth et al. | 433/119 |
| 3,526,219 | 9/1970 | Batamuth | 433/119 |
| 4,283,175 | 8/1981 | Nash | 433/119 |
| 4,496,321 | 1/1985 | Kumabe et al. | 433/119 |
| 4,708,653 | 11/1987 | Eichen et al. | 433/165 |
| 4,804,364 | 2/1989 | Dieras et al. | 433/86 |
| 5,188,531 | 2/1993 | Von Sutfin | 433/119 |

FOREIGN PATENT DOCUMENTS
61-22857 1/1986 Japan .
61-22858 1/1986 Japan .
61-22859 1/1986 Japan .

Primary Examiner—Richard K. Seidel
Assistant Examiner—Paul M. Heyrana, Sr.
Attorney, Agent, or Firm—Haverstock, Garrett & Roberts

[57] ABSTRACT

An ultrasonic cutter suitable for cutting a fixation dressing used for orthopedic treatment of affected body parts so as to remove the dressing from an orthopedically bandaged body part, wherein in order to ensure structural simplification as well as a safe and easy cutting operation, the ultrasonic cutter includes a cutting blade (4) which is provided with a cutting edge on a side face (4A) only thereof, the leading end portion (4B) of the cutting blade (4) being round in shape and being provided with no cutting edge.

14 Claims, 5 Drawing Sheets

ULTRASONIC CUTTER

Applicants hereby claim foreign priority benefits under 35 USC § 119 of corresponding Japanese patent application Serial No. (Hei) 3-114073, filed Apr. 17, 1991, and Japanese PCT patent application Serial No. PCT/JP92/00488, filed Apr. 17, 1992.

BACKGROUND OF THE INVENTION

1. Field Of The Invention

The present invention relates to an ultrasonic cutter and, more particularly, to an ultrasonic cutter suitable for cutting the fixation materials used in forming orthopedic cast type dressings for immobilizing the affected body parts of orthopedic patients.

2. Prior Art

Both plaster of Paris bandages which use plaster as a curing agent and synthetic cast bandages which use a synthetic resin as a curing agent are known fixation type materials used for the fixation, support, protection or correction of orthopedic injuries such as fractures, dislocations, sprains, deformities and so forth. Such fixation materials are formed in such a manner that, on an affected or injured body part, an under-wrap, which is usually a cotton bandage or a tubular bandage composed of cotton, polyester and so forth, is first wound or applied onto the affected body part and a plaster of Paris bandage or a synthetic cast bandage is then wound and hardened onto the under-wrap.

Such a fixation material needs to be partially or wholly cut off at some point in time during the treatment of the affected body part or when the affected part is cured. As the cutters used for cutting such fixation or cast type materials, there are known power cutters, wire type cutters, heated blade type cutters, and ultrasonic cutters. Of these known cutters, the power cutters, wire type cutters, and heated blade type cutters each have several drawbacks, whereas the ultrasonic cutter, which is constructed so as to cut the fixation material by use of a cutting edge vibrated by an ultrasonic vibrator, is small in size and light in weight; it makes no noise nor does it produce a harmful gas; and it gives no sensation of fear to the patient. Furthermore, the ultrasonic cutter can easily cut through either a plaster of Paris bandage or a synthetic cast bandage. Thus, the ultrasonic cutter is preferred.

However, the ultrasonic cutter has a very large cutting force so that there is the danger that if, during operation, the blade happens to touch the skin of the patient, however slight the touch may be, the skin of the patient may be heavily wounded. Thus, a preventive measure against such a danger must be taken. There have so far been proposed several methods wherein, according to each, the electrostatic capacity between the cutting blade and the skin is used as a factor for determining the oscillation frequency of an oscillator so that the vibration of the cutter is controlled by utilizing the variation caused in the oscillation frequency of the oscillator when the cutting blade comes close to the skin. See Japanese Unexamined Patent Application Publication Nos. Sho 61-22857, Sho 61-22858, Sho 61-22859. However, in this case, differences in the controlled vibration occur in accordance with the individual differences among patients and the kinds and states of the under-wrap used. Thus, a high reliability cannot always be obtained.

Moreover, a further method has been proposed by the present applicant, according to which a blade cover is provided so as to surround the cutting blade, the blade cover being displaceable in the longitudinal direction of the cutting blade so that the length of the cutting blade which projects from the blade cover is adjustable. In this situation, the fixation material is cut by the cutting blade with the leading end of the blade cover kept in contact with the surface of the fixation material thereby preventing the cutting blade from coming into contact with the skin. In this case, several drawbacks likewise exist. For example, it is difficult to adjust the exposed length of the cutting blade since the distance between the rear surface of the fixation material and the skin is not always constant. Also, since the cutting edge is formed extending as far as the leading end of the cutting blade, the cutting edge is apt to catch the under-wrap lying inside of the fixation material and thus, unless cutting even the under-wrap, the cutter blade cannot be moved forward anymore. As a result, since the bandage constructed with the under-wrap is of such a nature as to be hardly cut by the ultrasonic cutter, the cutting of the fixation material cannot be smoothly performed. In addition, since the cutting blade is surrounded by the blade cover, the operator cannot look straight at the cutting edge even if the blade cover is made of a transparent material. The handling of this type of cutter is not easy.

PROBLEMS TO BE SOLVED BY THE INVENTION

It is the object of the present invention to provide an ultrasonic cutter which is especially excellent in cutting an orthopedic fixation material of the type already mentioned, which cutter can cut the fixation material with safety and ease and, yet, is of a simple construction.

In order to achieve the above mentioned object, the ultrasonic cutter constructed according to the present invention comprises a tubular ultrasonic wave generator case, an ultrasonic wave generator housed within said case, and a cutting blade detachably mounted at one end of the ultrasonic wave generator so as to be projected from the case, a cutting edge being provided on a side face only of the cutting blade. The leading end portion of the cutting blade is made round and includes no cutting edge portion. More specifically, the leading end of the cutting blade can be, for instance, circular or oval in shape, or it can be made into any other outwardly convex smooth curve with no sharp angular portion.

In the ultrasonic cutter according to the present invention, the ultrasonic vibration produced by the ultrasonic wave generator housed in the case is applied to a cutting blade, whereby the cutting blade is vibrated so that, by contacting the cutting edge formed on a side face of the cutting blade with an object to be cut such as, for instance, an orthopedic fixation material, the fixation material can be cut. Therefore, even if during the cutting of the fixation material, the cutting blade sinks so that the leading end thereof comes into contact with the skin, the skin is not injured at all because the leading end portion of the cutting blade is round and includes no cutting edge. Moreover, the under-wrap which is usually provided under the plaster bandage is not caught by the cutting blade and thus, the cutting operation can be smoothly carried out. Furthermore, since the whole of the cutting blade is exposed, the operator can always look straight at the cutting blade and, therefore, the cutting operation can be done easily, and no sensation of fear is given to either the operator or the patient. In addition, if the ultrasonic cutter according to the present invention is constructed such that electric power is supplied thereto only while a switch is depressed, and, during this period, a sound signal is also produced, then enhanced safety can be assured.

Thus, according to the present invention, there can be provided a cutter which is very simple in construction yet safe in operation and, in addition, which possesses all the advantages inherent in this type of ultrasonic cutter.

DETAIL EMBODIMENTS OF THE INVENTION

Embodiments of the present invention will now be described by reference to the drawings.

Figure 1:
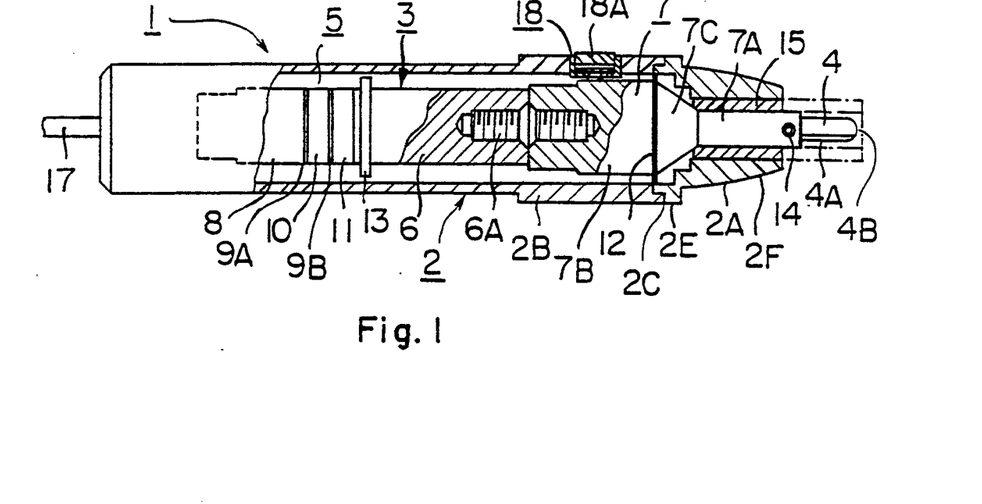
FIG. 1 is a partially cut-away, longitudinally sectioned side view showing an embodiment of the present invention.
Figure 2:
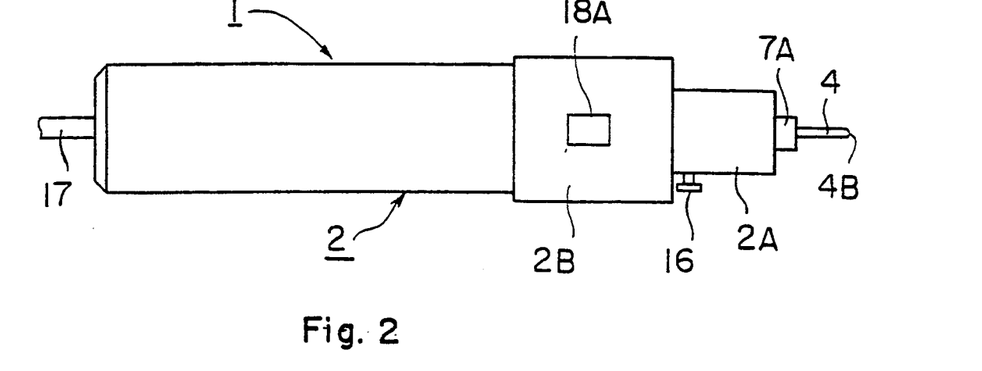
FIG. 2 is a top plan view of the embodiment of the present invention shown in FIG. 1.
Figure 3:
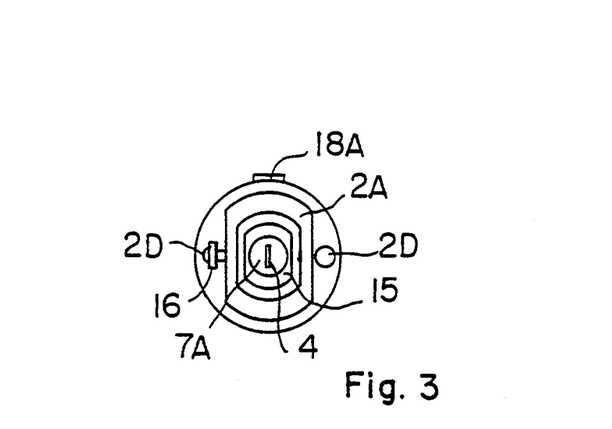
FIG. 3 is a right end view of the embodiment of the present invention shown in FIG. 1.
Figure 4A:
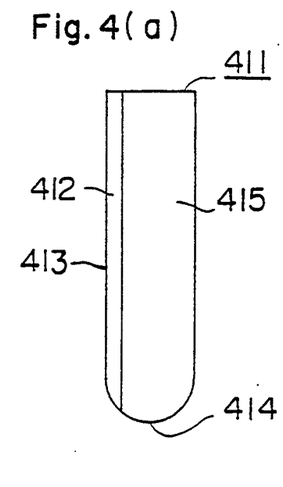
FIGS. 4(a), 4(b), 4(c) and 4(d) represent a front view, a left side view, a right side view, and a bottom plan view respectively of one embodiment of the cutting blade constructed according to the present invention.
Figure 4B:
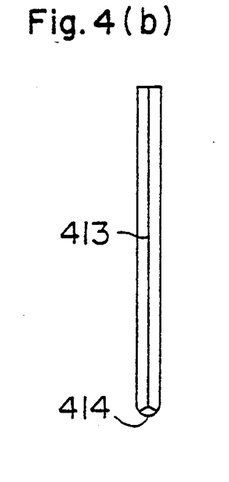
Figure 4C:
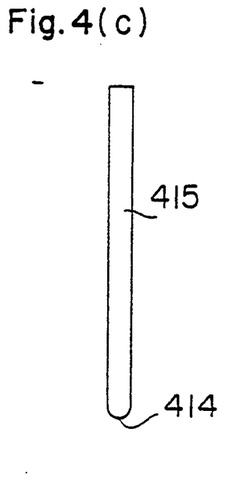
Figure 4D:
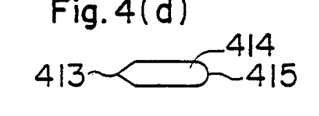
Figure 5A:
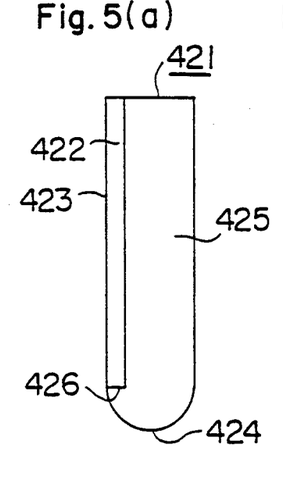
FIGS. 5(a), 5(b), 5(c) and 5(d) represent a front view, a left side view, a right side view, and a bottom plan view respectively of another embodiment of the cutting blade constructed according to the present invention.
Figure 5B:
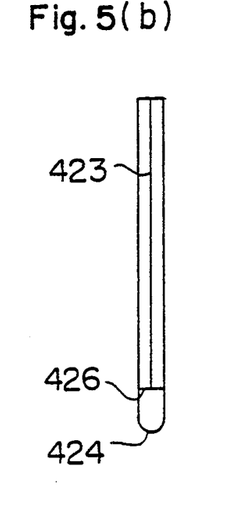
Figure 5C:
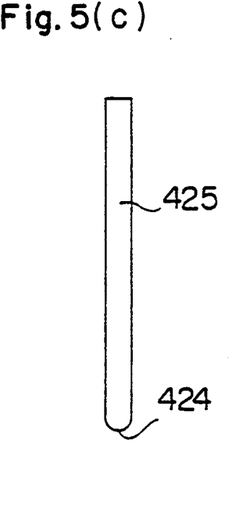
Figure 5D:
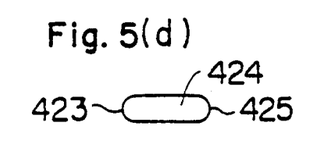

Referring to FIGS. 1, 2 and 3, an ultrasonic cutter 1 comprises a tubular case 2 for housing an ultrasonic wave generator 3 therein, and a cutting blade 4 detachably mounted at one end of the ultrasonic wave generator 3, namely, the right side end of the cutter shown in FIG. 1. The case 2 is constructed so as to be dividable into two portions, that is, a front case portion 2A and a rear case portion 2B. The two case portions 2A and 2B are constructed so as to be fitted to each other in the mutually opposed portion 2C thereof and coupled together by means of screws 2D (FIG. 3). The rear case portion 2B is formed into a generally cylindrical shape, while the front case portion 2A is constructed in such a manner that a portion 2E thereof facing the rear case portion 2B is cylindrically shaped, but its leading end portion 2F is formed with its mutually opposed faces cut so as to be parallel to each other as shown in FIG. 3.

The ultrasonic wave generator 3 is composed of an ultrasonic wave transducer 5 and a horn 7 coupled to the ultrasonic wave transducer 5 through a booster 6. The ultrasonic wave transducer 5 comprises an aluminium block 8, an electrode 9A, a first ceramic oscillator 10, an electrode 9B and a second ceramic oscillator 11 successively disposed in this order. These component members are fixed by means of a bolt (not shown) so as to be clamped from the end face at the side of the aluminium block 8 to the booster 6. That is, the ceramic oscillators 10 and 11 are held by and between the aluminium block 8 and the booster 6 through the electrodes 9A and 9B, thus constituting a so-called innerperiphery clamping type bolting Langevin type oscillator. The booster 6 has the function of amplifying the ultrasonic wave vibration produced by the ultrasonic wave generator 5 and transmitting it to the horn 7.

The horn 7 used in this case is of the construction in which a small-diameter portion 7A is disposed at one side, while a large-diameter portion 7B is provided at the other side. Between the two horn portions 7A and 7B, an intermediate portion 7C is formed in an exponential or conical shape. The horn 7 is fixed to the front side of the booster 6 by means of a stud bolt 6A. The boundary portion between the large-diameter horn portion 7B and the intermediate horn portion 7C corresponds to the position at which the amplitude of the ultrasonic wave (standing wave) produced by the ultrasonic wave transducer 5 is zero and in this portion, a flange 12 for securing the horn 7 to the case 2 is integrally provided. The flange 12 is fixed to the case in the portion 2C where the front case portion 2A and the rear case portion 2B face each other. The ultrasonic wave transducer 5 is held in approximately the center of the rear case portion 2B by the action of a flange 13 provided on the booster 6.

The cutting blade 4 is inserted into a deep groove (not shown) formed in the leading end portion of the horn 7 and is tightly fixed therein by means of a setscrew 14. The cutting blade 4 can be easily replaced with another when necessary. The cutting blade 4 has a cutting edge provided only on a side face 4A, the leading end 4B being made round and having no cutting edge.

Referring to FIG. 4, the cutting blade 411 has a sharp cutting edge 413 on one side face 412 thereof, the leading end 414 being formed round, having no cutting edge, and having exactly the same thickness as that of the main cutting-blade body. On the other side face 415 of the cutting blade 411, no cutting edge is likewise provided.

Referring to FIG. 5, the cutting blade 421 has a sharp cutting edge 423 on one side face 422 thereof, the leading end 424 being made round and has no cutting edge while the other side face 425 likewise has no cutting edge. In these respects, the cutting blade 421 of FIG. 5 is similar to the cutting blade shown in FIG. 4 but, in case of the cutting blade 421, the end 426 of the cutting edge 423 does not extend as far as the round-shaped leading end portion but, unlike the embodiment of FIG. 4, terminates at a point slightly short of the round-shaped leading end portion. Thus, the cutting blade of FIG. 5 is inadvantageous with respect to the manufacture thereof as compared with the manufacture of the cutting blade of FIG. 4, but the former is advantageous in that its safety is further enhanced.

Figures 6A, 6B, 6C, 6D:
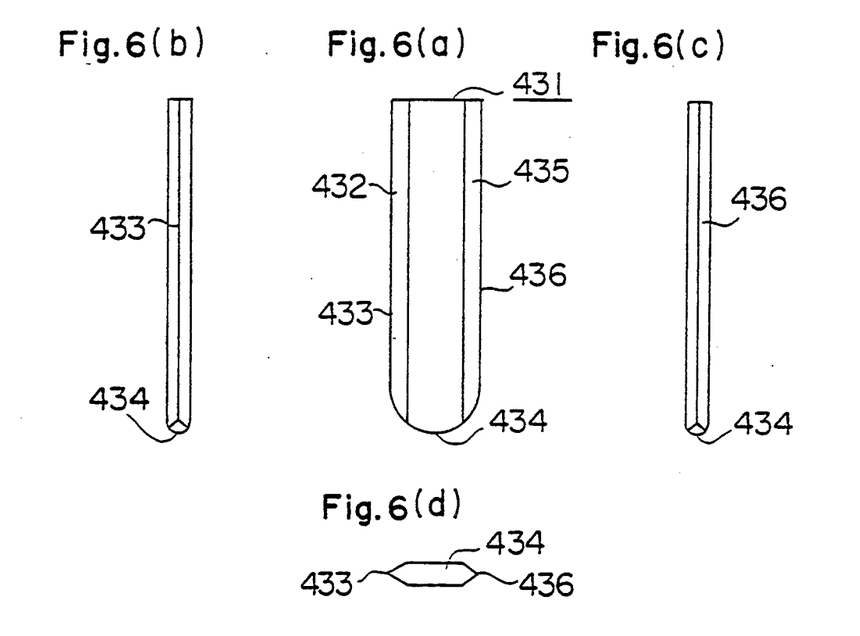
FIGS. 6(a), 6(b), 6(c) and 6(d) represent a front view, a left side view, a right side view, and a bottom plan view respectively of still another embodiment of the cutting blade constructed according to the present invention.

Referring to FIG. 6, the cutting blade 431 has a sharp cutting edge 433 on one side face 432 thereof, and the leading end 434 thereof is formed round and has no cutting edge. In these respects, this cutting blade is also similar to the cutting blade of FIG. 4, but, in case of cutting blade 431, a sharp cutting edge 436 is also provided on the other side face 435. Thus, in case of the cutting blade 431, both side faces alike can be used for cutting.

Figures 7A, 7B, 7C, 7D:
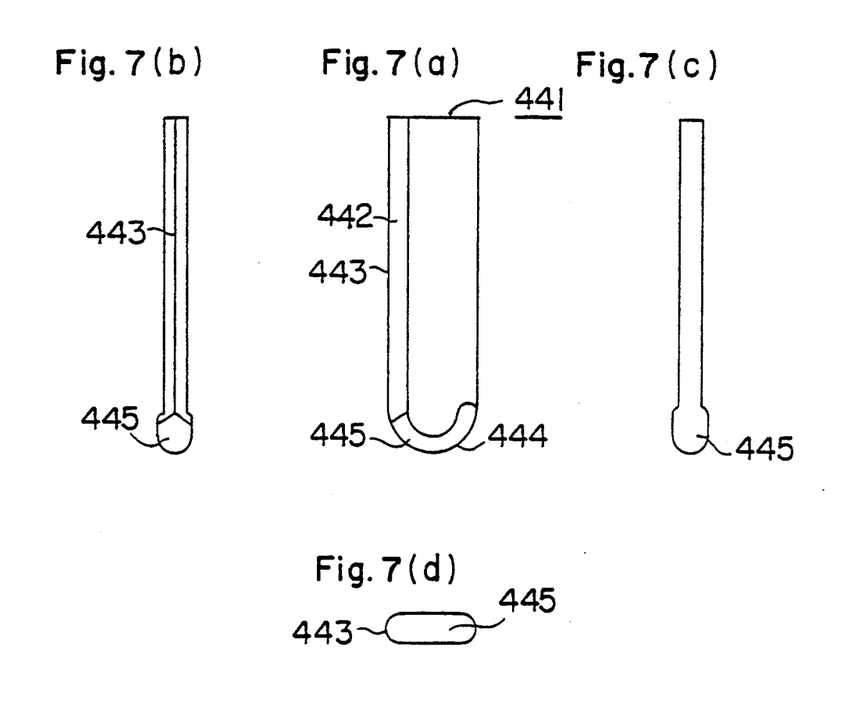
FIGS. 7(a), 7(b), 7(c) and 7(d) represent a front view, a left side view, a right side view, and a bottom plan view respectively of still another embodiment of the cutting blade constructed according to the present invention.
Figure 8A:
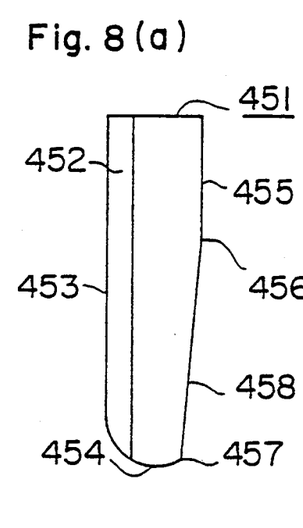
FIGS. 8(a), 8(b), 8(c) and 8(d) represent a front view, a left side view, a right side view and a bottom plan view respectively of a still further embodiment of the cutting blade constructed according to the present invention.
Figure 8B:
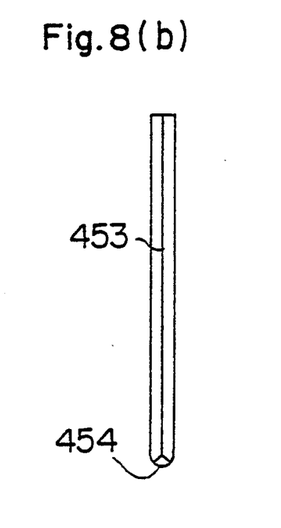
Figure 8C:
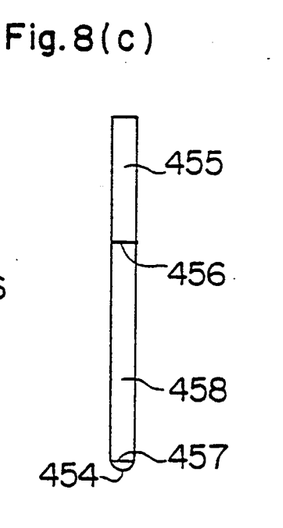
Figure 8D:
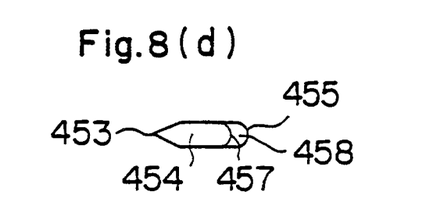

Referring to FIG. 7, the cutting blade 441 has a sharp cutting edge 443 on one side face 442 thereof, and the leading edge 444 is again formed round and has a bulged portion 445 which has a thickness greater than that of the main cutting-blade body. This enhances the safety of the leading end portion.

Referring to FIG. 8, the cutting blade 451 has a sharp cutting edge 453 on one side face 452 thereof, and the leading end 454 is again made round and has no cutting edge. In these respects, this cutting blade 451 is similar to that of FIG. 4. The other end face 455 of cutting blade 451 likewise has no cutting edge and, in addition, the portion 458 between an intermediate position 456 and the leading end 457 is tapered. By so doing, the cutting blade 451 is reduced in weight; the load applied to the mounting portion of the cutting blade during vibration is decreased so that the possibility that the cutting blade may slip off or be broken can be minimized.

If the cutting blade is too thick, the cutting force and the frictional resistance increase so that, due to the resulting heat development, a burn is caused, and therefore, the thickness of the cutting blade is selected to be about 0.8 mm or less and, preferably, 0.4 mm. If the width of the cutting blade is too large, similarly the cutting resistance and the frictional resistance are increased so that, due to the heat developed, a burn is caused. Moreover, curve-cutting or bend-cutting becomes difficult. Further, if the width of the cutting blade is too narrow, safety becomes inferior due to the fact that the texture of the cast is coarse, and the strength of the blade is inferior. Thus, the width is selected to be about 1 mm to 10 mm and, preferably about 4 mm. High-speed steel, carbon steel or the like can be used as the material for the cutting blade.

In each of the foregoing embodiments of the present invention, the leading end of the cutting blade is made round, but it can likewise be made into a different curved shape such as, for instance, an oval shape. In short, it suffices if the leading end of the cutting blade is only smoothly curved with no angular portion capable of catching or hooking anything.

Inside of the front case 2A, a cutting blade cover 15 is disposed so as to be reciprocatingly movable along the longitudinal direction of the front case portion 2A. A finger grip 16 mounted on the cutting blade cover 15 is moved in and along a groove (not shown) provided in the front case portion 2A, whereby the cutting cover 15 can be drawn into the front case portion 2A to an operating position at which the cutting blade is exposed as shown in FIG. 1, or the cutting blade 15 can be drawn out from the front case portion 2A and brought to a protective position shown by dot-and-dash lines in FIG. 1, at which position the cutting blade 4 is completely covered thereby. In this situation, it is advantageous to have a locking mechanism which would hold the cutting blade cover 15 at its operating and protective positions, respectively.

The electrodes 9A and 9B of the ultrasonic wave transducer 5 are connected to an oscillation circuit through a lead wire 17 which extends out from the rear end of the rear case portion 2B so that the high-frequency output produced by the oscillation circuit is fed to the cutter, whereby the ceramic oscillators 10 and 11 convert the thus caused electric oscillation into a mechanical vibration to thereby produce an ultrasonic wave.

Figure 9:
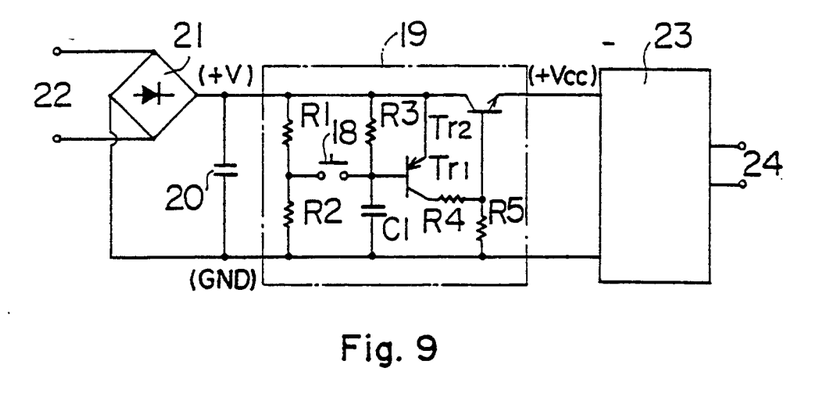
FIG. 9 is a connection diagram showing an embodiment of the electric switch circuit used in the present invention.

On the upper surface portion of the rear case portion 2B, which portion lies near the leading end, a switch 18 is provided. This switch 18 is for opening or closing a switch circuit 19 as shown in FIG. 9. The switch circuit 19 is connected to a power source 22 through a smoothing capacitor 20 and rectifier means 21 and comprises resistors R1, R2, R3, R4 and R5, a capacitor C1, and transistors Tr1 and Tr2. A switch 18 is connected between the junction point of the resistors R1 and R2 and the base of the transistor Tr1, and both resistors R1 and R2 divide a supply DC voltage (+V). By suitably selecting the resistance values of the resistors R1 and R2, the voltage across the switch 18 when the switch 18 is in its OFF state can be set at several V to ten and odd V even if the supply DC voltage is a high voltage which is higher than 140 V. Thus, a small switch can be used as the switch 18. By closing the switch 18, the transistor Tr1 is made conductive whereby the transistor Tr2 is made conductive so that a supply voltage (+Vcc) can be applied to an oscillation circuit 23 connected to the output side of the switch circuit 19. An output end 24 of said oscillation circuit 23 is connected to the external lead wire 17 of the ultrasonic wave transducer 5.

The switch 18 used in this case is of a simple construction and includes a spring (not shown) located beneath the switch button 18A as shown in FIG. 1 for urging the switch button 18A upwardly. Due to this construction, it is ensured that, only while the switch button 18A is depressed, the circuit is closed to supply power to the ultrasonic wave generator 3 so as to vibrate the cutting blade 4. Thus, this construction is excellent for safety reasons.

Figure 10:
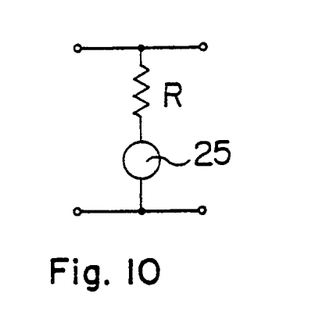
FIG. 10 is a connection diagram showing an embodiment of the sound generator used in the present invention.

Further, it is also possible to incorporate into the switch circuit 19, a sound generator operatively associated with the switch 18 so that, while the switch button 18A is depressed, a sound is produced to indicate that operation is under way, informing or alarming that the cutting blade is in its cuttable state. FIG. 10 shows an embodiment comprising such a circuit arrangement wherein a flicker buzzer 25 is connected to the output end of the switch circuit 19 shown in FIG. 9 through a current limiting resistor R, and a DC voltage of about 2 to 5 V obtained by thus dropping the supply voltage is applied to the buzzer.

Figure 11:
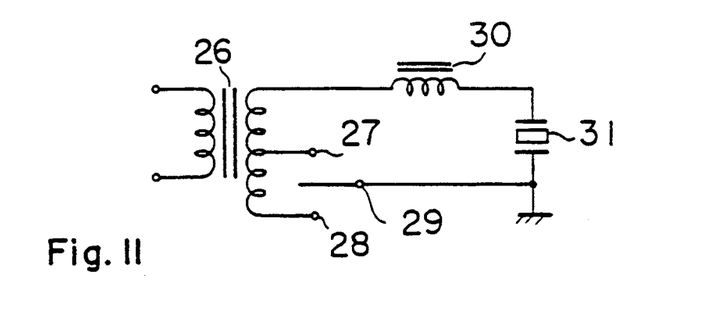
FIG. 11 is a connection digram showing an embodiment of the output changeover circuit used in the present invention.

Various fibers such as cotton fiber, glass fiber, polyester fiber and so forth are commonly used as the base fabric for plaster of Paris bandages or synthetic cast bandages. The cutting forces suitable for cutting these various fibers differ depending upon the type of fibers being used. For instance, in the case where a glass fiber is used for the base fabric, if the cutting output is too large, there is the fear that heat may be generated to cause a burn and, since the resin of the plastic cast sticks, the cutting ability lowers and, therefore, a low output is used. In the case of a polyester fiber, if the cutting output is too small, it becomes difficult to effect cutting so that it is required to provide a high output. It is therefore desirable to construct the system in such a manner that the output of the oscillation circuit can be switched over into several stages so that the cutting force can be adjusted. FIG. 11 shows an embodiment comprising such a system arrangement wherein, on the secondary side of the output transformer 26 of the oscillation circuit 23 shown in FIG. 9, taps 27 and 28 are provided so that, by means of a selector switch 29, changeover is effected between the tap 27 (low output) and the tap 28 (high output) and, through a choke coil 30, the oscillation output is applied to an ultrasonic vibrator 31.

In the case where a plaster of Paris bandage is to be cut by use of the ultrasonic cutter of this invention which is constructed as described above, the cutting blade cover 15 is drawn back into the front case portion 2A by use of the finger grip 16 so as to expose the cutting blade 4. The switch 18 is then manipulated whereby the cutting blade 4 is caused to vibrate, thus getting into a cuttable state. If that side face of the cutting blade 4 on which the cutting edge is provided is now contacted with the surface of the bandage and, in this state, the cutting blade 4 is moved, the cutting of the bandage is effected very easily. Moreover, by selecting the thickness of the cutting edge 4 to be about 0.4 mm, the under-wrap or the skin, which has elasticity, cannot completely absorb the energy produced from the cutting edge so that, even if the cutting blade sinks deep into the surface of the bandage and thus the leading end portion of the cutting blade comes into contact with the skin, it is ensured that, unless the cutting blade is excessively inclined and, as a result, the side face portion of the cutting blade on which the cutting edge is provided touches the skin, an accidental cutting of the skin will not occur.

Upon completion of the cutting operation, the finger depressing the switch button 18A is released therefrom, whereby the vibration of the cutting blade 4 is immediately stopped. The cutting blade cover 15 is then drawn out from the front case portion 2A by use of the finger grip 16, whereby the cutting blade 4 is again covered by the cover 15 and thus protected against any external impact inflicted thereon.

Thus there has been shown and described novel means for an ultrasonic cutter, which invention fulfills all the objects and advantages set forth above. It will be apparent to those skilled in the art, however, that many changes, modifications, variations and other uses and applications of the present invention are possible. All such changes, modifications, variations and other uses and applications which do not depart from the spirit and scope of the invention are deemed to be covered by the invention which is limited only the claims which follow.

What is claimed:

1. An ultrasonic cutter comprising a tubular ultrasonic wave generator case, an ultrasonic wage generator housed in said case, and a cutting blade detachably mounted at one end of said ultrasonic wave generator so as to be capable of projecting from said case, said cutting blade being formed into a flat sheet shape and having a cutting edge provided only on a side face thereof, the leading end portion of said cutting blade being formed round and having no cutting edge.

2. An ultrasonic cutter comprising a housing assembly, an ultrasonic wave generator positioned and located within said housing assembly, a relatively thin elongated cutting blade detachably mounted to said ultrasonic wave generator so as to project exterior of said housing assembly, said cutting blade being substantially planar and straight along its entire length and extending exterior of said housing assembly in a direction either along or parallel to the longitudinal axis of said housing assembly, said cutting blade having a terminal end portion and at least one side face associated therewith, the side face only of said cutting blade having a cutting edge associated therewith, the terminal end portion of said cutting blade having a smoothly curved non-cutting surface associated therewith, and means enabling said ultrasonic wave generator to vibrate said cutting blade so as to effect a cutting action when the cutting edge of said blade is positioned against a surface to be cut.

3. The ultrasonic cutter defined in claim 2 wherein the terminal end portion of said cutting blade is substantially round in shape.

4. The ultrasonic cutter defined in claim 2 wherein the cutting edge associated with the side face of said cutting blade extends along only a portion of said side face and terminates at a point short of the terminal end portion thereof.

5. The ultrasonic cutter defined in claim 2 wherein the terminal end portion of said cutting blade has a thickness greater than the thickness associated with the remainder of said cutting blade.

6. The ultrasonic cutter defined in claim 2 wherein said cutting blade includes a side face opposite said cutting edge, said opposed side face likewise having a cutting edge associated therewith.

7. The ultrasonic cutter defined in claim 2 wherein said cutting blade includes an opposed side face, said opposed side face having at least a portion thereof tapered, said taper portion extending from an intermediate location along said opposed side face to the terminal end portion of said cutting blade.

8. The ultrasonic cutter defined in claim 2 including a cover member for shielding said cutting blade when not in use, said cover member extending along the longitudinal direction of said cutting blade and being reciprocatingly movable between a first operative position wherein said cover member is positioned so as to expose said cutting blade for use and a second closed position wherein said cover member is positioned so as to completely cover said cutting blade.

9. The ultrasonic cutter defined in claim 8 including means for facilitating the movement of said cover member between its first and second positions.

10. The ultrasonic cutter defined in claim 8 including locking means for holding and maintaining said cover member in its respective first and second positions.

11. The ultrasonic cutter defined in claim 2 wherein said means enabling said wave generator to vibrate said cutting blade includes switch means for electrically supplying power to said ultrasonic wave generator, said switch means being positionable to an "off" position wherein no electrical power is supplied to said wave generator and to an "on" position wherein electrical power is supplied to said wave generator.

12. The ultrasonic cutter defined in claim 11 including sound generator means operatively connected to said switch means whereby when said switch means is positioned to its "on" position said sound generator means produces an audible sound indicating that said cutting blade is being vibrated for operative use to effect a cutting action.

13. The ultrasonic cutter defined in claim 2 including means for varying the vibratory motion of said cutting blade.

14. An ultrasonic cutter suitable for cutting a fixation type dressing used for orthopedic treatment of an affected body part comprising a substantially tubular outer case member, an ultrasonic wave generator for producing an ultrasonic wave vibration housed within said tubular case member, a cutting blade including means for removably attaching the same to said ultrasonic wave generator, said cutting blade being substantially flat and straight along its entire length and extending exteriorly of said tubular case member in a direction along the longitudinal axis of said tubular case member, said cutting blade having a smoothly shaped terminal end portion and at least one side face associated therewith, a cutting edge extending along at least a portion of the side face of said cutting blade, means for supplying electrical power to said wave generator, means for amplifying the ultrasonic wave vibration produced by said wave generator and transmitting the same to said cutting blade so as to effect a cutting action, switch means for controlling the supply of electrical power to said wave generator, sound generator means for producing an audible sound when said switch means is activated, and means for varying the cutting force transmitted to said cutting blade when electrical power is supplied to said wave generator.

\* \* \* \* \*

UNITED STATES PATENT AND TRADEMARK OFFICE
CERTIFICATE OF CORRECTION

PATENT NO. : 5,355,587
DATED : October 18, 1994
INVENTOR(S) : Naomitsu Takekawa, et al It is certified that error appears in the above-indentified patent and that said Letters Patent is hereby corrected as shown below:

Column 7, line 59, "wage" should be --wave--.

Signed and Sealed this

Sixth Day of December, 1994

Attest:

BRUCE LEHMAN

*Attesting Officer*  *Commissioner of Patents and Trademarks*